(12) United States Patent
Friman et al.

(10) Patent No.: US 11,480,636 B2
(45) Date of Patent: Oct. 25, 2022

(54) OPTICAL DATA CABLE HANDLING ON PATIENT TABLE OF MRI SYSTEM

(71) Applicant: KONINKLIJKE PHILIPS N.V., Eindhoven (NL)

(72) Inventors: Olli T. Friman, Eindhoven (NL); Tracy Wynn, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 795 days.

(21) Appl. No.: 15/528,524

(22) PCT Filed: Nov. 10, 2015

(86) PCT No.: PCT/IB2015/058655
§ 371 (c)(1),
(2) Date: May 22, 2017

(87) PCT Pub. No.: WO2016/083926
PCT Pub. Date: Jun. 2, 2016

(65) Prior Publication Data
US 2017/0269177 A1 Sep. 21, 2017

Related U.S. Application Data

(60) Provisional application No. 62/083,671, filed on Nov. 24, 2014.

(51) Int. Cl.
*G01R 33/34* (2006.01)
*G01R 33/36* (2006.01)
(Continued)

(52) U.S. Cl.
CPC .............. *G01R 33/34* (2013.01); *A61B 5/055* (2013.01); *G01R 33/307* (2013.01);
(Continued)

(58) Field of Classification Search
CPC .............. G01R 33/34; G01R 33/34007; G01R 33/307; G01R 33/3692; G01R 33/385;
(Continued)

(56) References Cited

U.S. PATENT DOCUMENTS

4,264,235 A * 4/1981 Reed .................... E21B 43/0107
405/164
D267,776 S * 2/1983 Holgersson .................. D25/121
(Continued)

FOREIGN PATENT DOCUMENTS

| JP | 0440939 A | 2/1992 |
|---|---|---|
| JP | 2008005954 A | 1/2008 |
| WO | 2005045296 A1 | 5/2005 |

*Primary Examiner* — Peter M. Cuomo
*Assistant Examiner* — Morgan J McClure (57) ABSTRACT

An arrangement and system places an external cable into a slot. The arrangement includes a slot extending from a first end to a second end. The slot includes a recess configured to receive a cable therein. The arrangement includes a movable component configured to slide along a length of the slot. The movable component includes a first end and a second end. Sliding the movable component along the slot in a first direction from the first end to the second end of the slot one of frees a first portion of the cable from the slot or places a second portion of the cable in the slot.

23 Claims, 8 Drawing Sheets

(51) Int. Cl.
*A61B 5/055* (2006.01)
*G01R 33/30* (2006.01)
*G01R 33/385* (2006.01)
*A61B 90/11* (2016.01)
*E21B 43/01* (2006.01)
*A61B 90/00* (2016.01)

(52) U.S. Cl.
CPC ....... *G01R 33/3692* (2013.01); *G01R 33/385* (2013.01); *A61B 90/00* (2016.02); *A61B 90/11* (2016.02); *E21B 43/01* (2013.01)

(58) Field of Classification Search
CPC ....... A61B 90/00; A61B 90/11; A61B 5/0555; E21B 43/01
See application file for complete search history.

(56) References Cited

U.S. PATENT DOCUMENTS

| | | | | |
|---|---|---|---|---|
| 5,065,760 | A * | 11/1991 | Krause | A61B 5/04286 324/318 |
| D355,582 | S * | 2/1995 | Sleight | D8/354 |
| 5,474,068 | A * | 12/1995 | Takamori | A61B 6/56 242/378.2 |
| D443,198 | S * | 6/2001 | Snyder | D25/164 |
| 7,467,004 | B2 * | 12/2008 | Calderon | A61G 7/1019 5/600 |
| D753,605 | S * | 4/2016 | McPherson | D13/155 |
| 2005/0218269 | A1 | 10/2005 | Franks | |
| 2007/0044988 | A1 * | 3/2007 | VanderVelde | H02G 3/0418 174/72 A |
| 2007/0138349 | A1 | 6/2007 | Ayoub | |
| 2007/0144760 | A1 * | 6/2007 | VanderVelde | H02G 3/0418 174/72 A |
| 2008/0163425 | A1 * | 7/2008 | White | A61G 7/0503 5/603 |
| 2009/0306495 | A1 * | 12/2009 | Scarth | G01R 33/307 600/415 |
| 2010/0031443 | A1 * | 2/2010 | Georgiev | A61B 5/0555 5/601 |
| 2012/0118630 | A1 * | 5/2012 | Jiang | G01R 33/36 174/74 R |
| 2013/0000097 | A1 * | 1/2013 | Pino | H02G 3/0431 29/428 |
| 2013/0131497 | A1 * | 5/2013 | Linz | A61B 5/0555 600/415 |
| 2014/0031671 | A1 * | 1/2014 | Friman | G01R 33/30 600/415 |
| 2015/0047125 | A1 * | 2/2015 | Bae | A61B 6/0407 5/601 |

\* cited by examiner

OPTICAL DATA CABLE HANDLING ON PATIENT TABLE OF MRI SYSTEM

CROSS REFERENCE TO RELATED APPLICATIONS

This application is a U.S. national phase application of International Application No. PCT/IB2015/058655, filed on Nov. 10, 2015, which claims the benefit of U.S. provisional Application Ser. No. 62/083,671 filed on Nov. 24, 2014 and is incorporated herein by reference.

Imaging devices such as a magnetic resonance imaging (MRI) device may utilize a variety of external cables for any number of reasons such as connecting an electronic component to another component. The imaging device is used to visualize internal structures of a body. For example, the MRI device may use nuclear magnetic resonance to image nuclei of atoms inside the body. The data gathered from using this technique may provide a basis in which an anatomical image may be generated. To generate the image, the MRI device may utilize a magnet to generate a magnetic field as well as gradient coils to generate an oscillating magnetic field applied at an appropriate resonant frequency. The magnet and gradient coils may be housed within the MRI device itself. The excited atoms may emit radio frequency signals that are registered on receiver coils. The receiver coils may be included in a coil panel that is placed over a patient near an area of interest while the patient is within a bore of the MRI device. This coil panel may be connected to the MRI device via one or more external cables.

Similar to any scenario in which an external cable is used, a person such as the technician or the patient may inadvertently displace the cable. For example, while the patient is moving into position onto a patient table of the MRI device, the patient may hook the cable. When sufficient force is applied to the external cable, the coil panel may become disconnected from the MRI device. In a worse scenario, the external cable, the MRI device, and/or the coil panel may suffer damage and render the MRI device unusable until fixed.

To compensate for these possibilities of using the external cable, the connection including the point in which the external cable is coupled to the coil panel, the point in which the external cable is coupled to the MRI device, and the external cable itself may be housed in a covering that is often sturdy such that the necessary force required to cause damage is unlikely to occur from the inadvertent movements of the person. However, although providing adequate protection, this manner of providing the external cable has many drawbacks such as being limited to a particular length of the cable as well as difficulty in maneuvering the coil panel as desired. That is, there is little to no flexibility in using the external cable.

The exemplary embodiments relate to an arrangement and system for placing an external cable into a slot. The arrangement comprises a slot extending from a first end to a second end, the slot including a recess configured to receive a cable therein; and a movable component configured to slide along a length of the slot, the movable component including a first end and a second end, wherein sliding of the movable component along the slot in a first direction from the first end to the second end of the slot one of frees a first portion of the cable from the slot or places a second portion of the cable in the slot.

The exemplary embodiments may be further understood with reference to the following description of the exemplary embodiments and the related appended drawings, wherein like elements are provided with the same reference numerals. The exemplary embodiments are related to an arrangement and system of placing an external cable into a slot to prevent damage to the cable and maintain the connections the external cable provides between two components. Specifically, the external cable may be flexible with a connector on a first end and a second end of the external cable coupled to a first component. The connector of the first end may subsequently couple to a further component. While in use, the external cable may be removed from the slot whereas the external cable may be placed within the slot for protection when not in use. The arrangement, the slot, the external cable, the connector, and the protection mechanism will be explained in further detail below.

The exemplary embodiments are described herein with respect to a magnetic resonance imaging (MRI) device. However, it should be noted that the MRI device is only exemplary. Specifically, the exemplary embodiments may be used in any scenario in which an external cable is used. Furthermore, it should be noted that the external cable being used with regard to electrically connecting two electronic components is also only exemplary. Specifically, the external cable may be used in any scenario in which one component or object is connected or tethered to another component or object. Therefore, although the exemplary embodiments herein relate exclusively to the MRI device and connecting a first electronic component to the MRI device, those skilled in the art will understand that the exemplary embodiments may also apply to a variety of different connections between two components regardless of whether the components are electronic or not.

Figure 1:
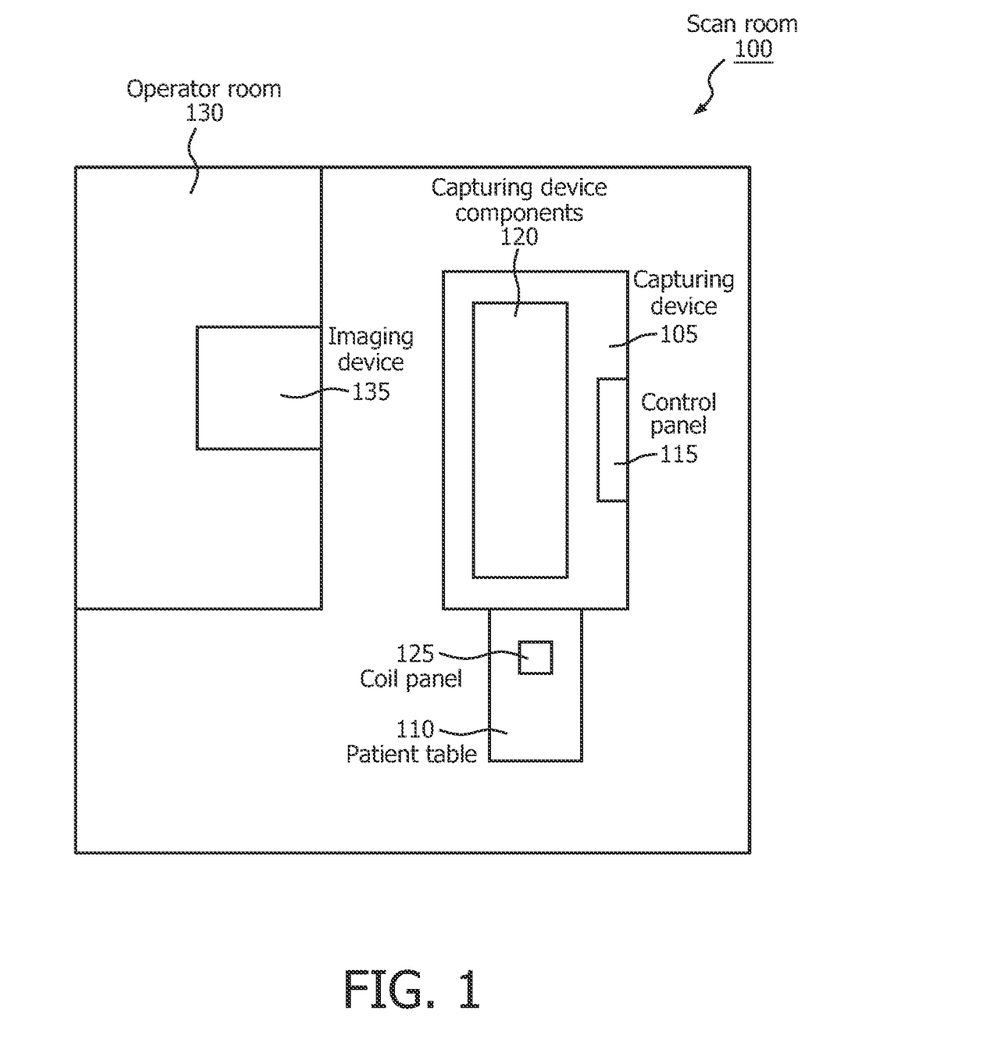
FIG. 1 shows a system for a scan room according to the exemplary embodiments.

FIG. 1 shows a system for a scan room 100 according to the exemplary embodiments. The scan room 100 is used for a patient who requires an imaging to be performed. For example, the patient may require a MRI to be performed on a specific body portion. The scan room 100 includes a capturing device 105 which has a patient table 110, a control panel 115, and capturing device components 120 as well as an operator room 130 including an imaging device 135.

According to the exemplary embodiments, the capturing device 105 may perform the scan on a patient lying on the patient table 110. Specifically, the capturing device 105 may be a MRI device. The capturing device 105 may utilize the capturing device components 120 to perform the scan. Accordingly, the capturing device components 120 may include corresponding types of components associated with the MRI device (e.g., magnetic coils). The patient may be moved within a bore of the capturing device 105 via inputs received on the control panel 115. The control panel 115 may allow an operator to move the patient table 110 for an alignment to be performed where the patient table 110 is moved to the isocenter (the point in space through which the central beam of radiation is to pass).

Those skilled in the art will understand that the patient table 110 is retractable. The patient is moved within the capturing device 105 such that a large, powerful magnet generates a magnetic field that is used to align the magnetization of some atomic nuclei in the body, and radio frequency magnetic fields (via gradient coils) are applied to systematically alter the alignment of this magnetization. This causes the nuclei to produce a rotating magnetic field detectable by the scanner (via receiver coils). This information is recorded to construct an image of the scanned area of the body.

In view of the mechanism used by the capturing device 105, the capturing device components 120 may include a variety of components such as a magnet, gradient coils, radio frequency (RF) coils, and receiver coils. As discussed above, the magnet produces a strong magnetic field around an area to be imaged for the imaging procedure. This magnetic field allows nuclei (e.g., hydrogen nuclei of water molecules) to align with a direction thereof. The gradient coils may be disposed within the magnet to produce a gradient in the magnetic field in various directions (e.g., X, Y, and Z).

The capturing device 105 may utilize different configurations in which the gradient coils and the receiver coils are arranged for the MRI device. In a first configuration, the capturing device 105 may have all the various coils within a housing of the capturing device 105 itself. When such a configuration is used, the patient is simply moved within the bore of the MRI device for the imaging to be performed. Specifically, the receiver coil may be disposed within the gradient coils to produce a further magnetic field necessary to rotate the spins by various angles (e.g., 90°, 180°, etc.) selected by a pulse sequence. Thus, a radio frequency signal emitted by excited hydrogen atoms in the body may be detected using the energy from the oscillating magnetic field applied at the appropriate resonant frequency. The orientation of the image may be controlled by varying the magnetic field produced by the magnet using the gradient coils and a contrast between tissues is determined by a rate at which the excited nuclei return to an equilibrium state. Specifically, the receiver coils may receive these energy measurements and provide the data to the imaging device 130 for processing to ultimately generate the images of the scan.

In a second configuration, the capturing device 105 may have a digital interface for the receiver coils that are housed within a coil panel 125 that is placed in close proximity to the area of interest on the patient. This coil panel 125 may therefore be positioned over a patient's chest, arm, leg, knee, etc. With the coil panel 125 positioned closer to the area of interest, it may be possible for more reliable radio frequency signals to be measured for the imaging to be performed. However, to properly utilize the receiver coil that is in the coil panel 125, an appropriate amount of power is required to be supplied in addition to a connection for the measured radio frequency signals to be transmitted.

The power may be provided through a power cable. However, the power cable succumbs to the various drawbacks discussed above such as inadvertent displacement and/or damage. It is also noted that the power cable may also utilize conducting materials that are subject to magnetism. Therefore, the covering of the power cable must also shield the power cable from the magnetic fields generated by the capturing device 105. To eliminate the need of the power cable, high capacity storage units occupying a limited space such as lithium batteries may be used. That is, the lithium batteries may store the necessary power to allow sufficient and feasible power storage for using the receiver coils. In this manner, the capturing device 105 only requires the connection for the measured radio frequency signals to be transmitted. To overcome the magnetism issue, this connection may be provided via an optical cable connection that does not include any electrically conductive materials and is therefore safe and indifferent to magnetic and electrical fields of the capturing device 105.

The use of the optical cable connection may overcome various issues but those skilled in the art will understand that use of an optical data cable entails handling considerations that are not necessarily safety related but more reliability and ergonomics related. Specifically, because the optical data cable utilizes light in transmitting the information, a steady path from one end to the other end must be maintained. Any damage along this path such as a bend or kink may prevent the information from being transmitted (whereas metallic wire cables may have bends and still transmit data so long as there is no break in the path). However, with only a requirement for an optical cable connection, a variable length may be provided for the coil panel 125 because a sturdy covering that would otherwise be used is not needed. Those skilled in the art will also appreciate that the optical cable connection occupies little space.

Because the optical data cable is still an external cable that may be subject to some of the drawbacks discussed above, the exemplary embodiments provide an arrangement for a user to handle and store the optical data cable in an appropriate location where it is always available and practically invisible and undetectable for the patient. That is, the patient has a very low probability of interacting with the optical data cable when stored, inadvertent or otherwise. As will be described in further detail below, the exemplary embodiments include a thin horizontal slot in which the optical data cable may be housed when not being used and released therefrom when being used. The exemplary embodiments may further include a slider that when moved in a first direction along the slot, aligns and guides the optical cable into the slot or when moved in a second opposite direction along the slot, releases the optical cable from the slot.

Figure 2:
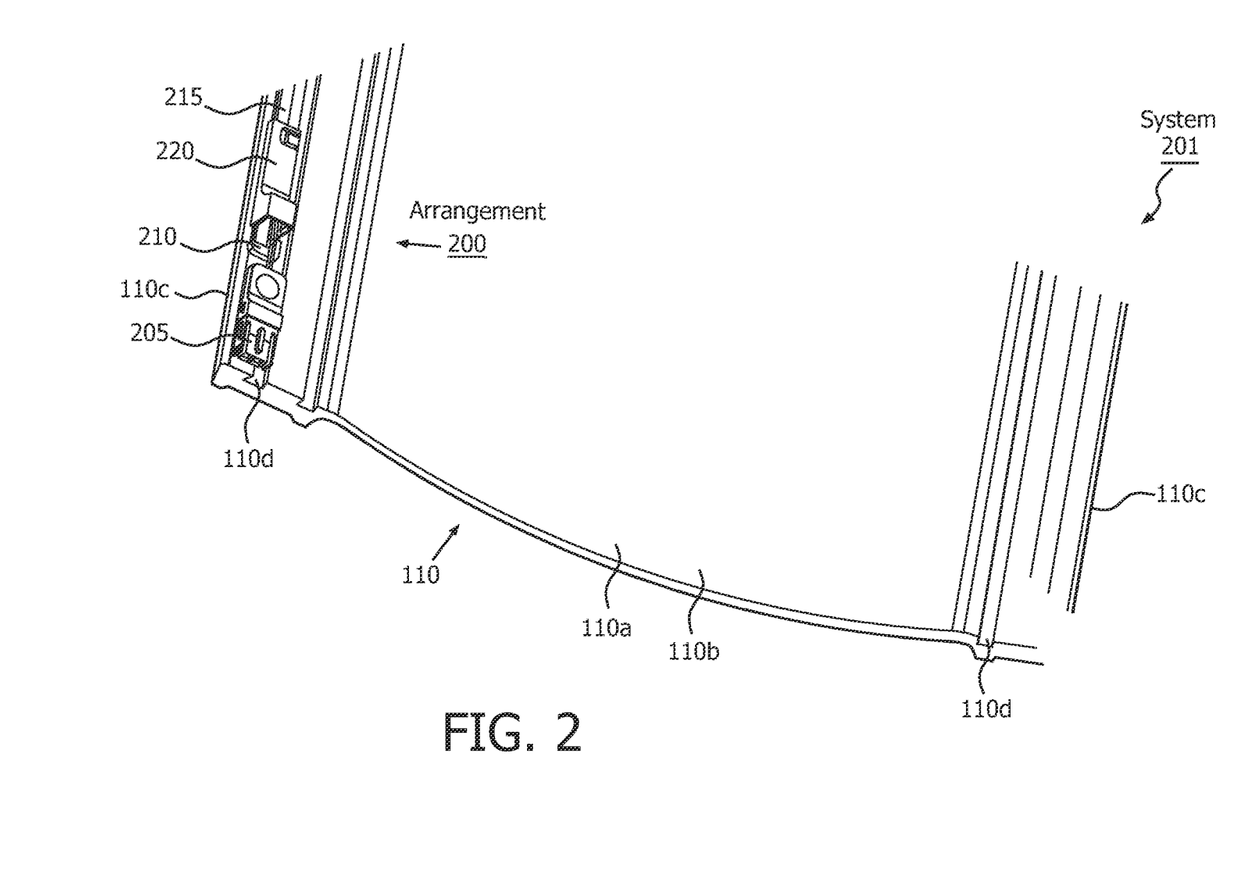
FIG. 2 shows an overall view of an arrangement incorporated into a patient table according to the exemplary embodiments.
Figure 3:
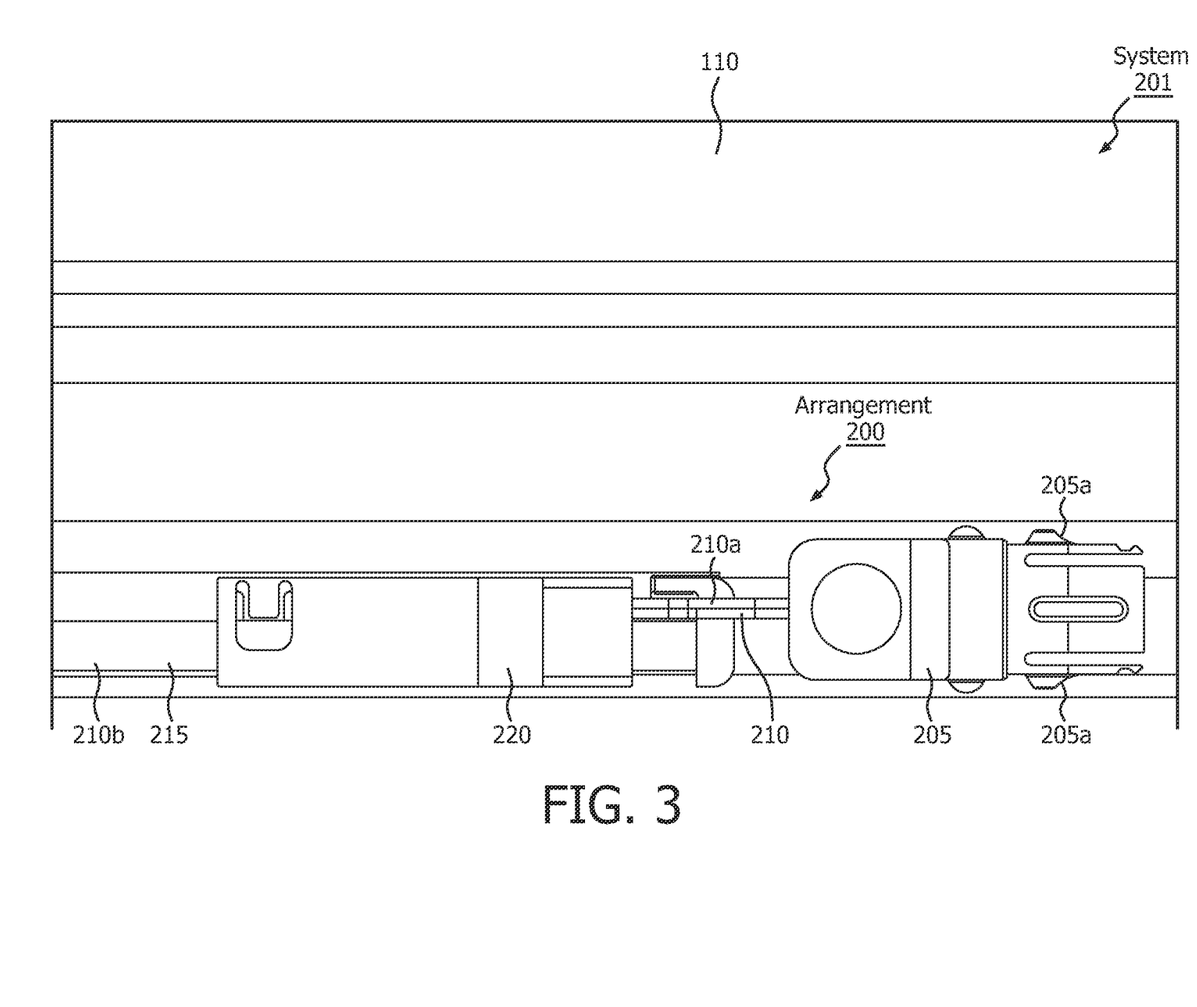
FIG. 3 shows an overhead view of the arrangement of FIG. 2 according to the exemplary embodiments.
Figure 4:
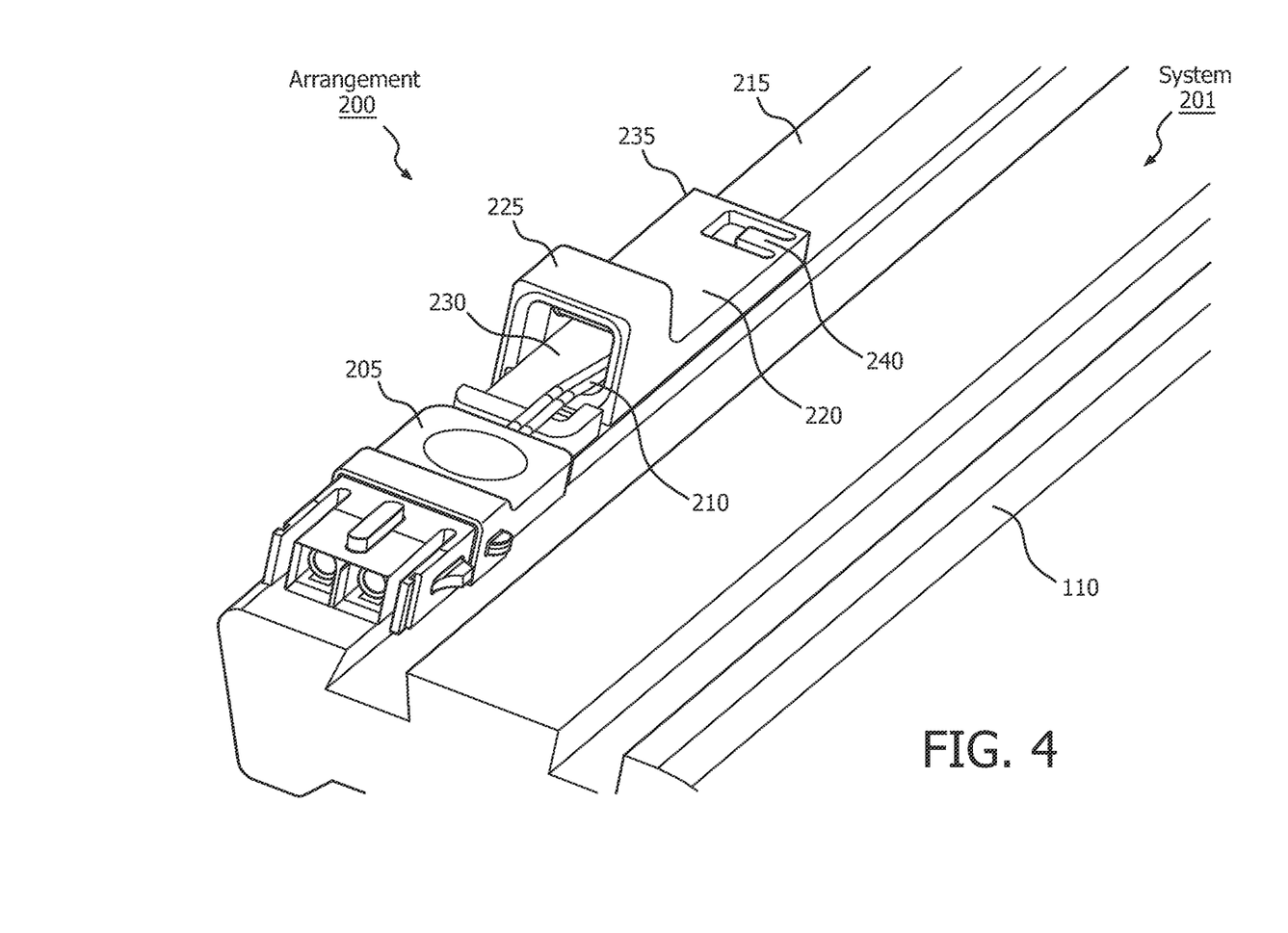
FIG. 4 shows a first perspective view of the arrangement of FIG. 2 according to the exemplary embodiments.
Figure 5:
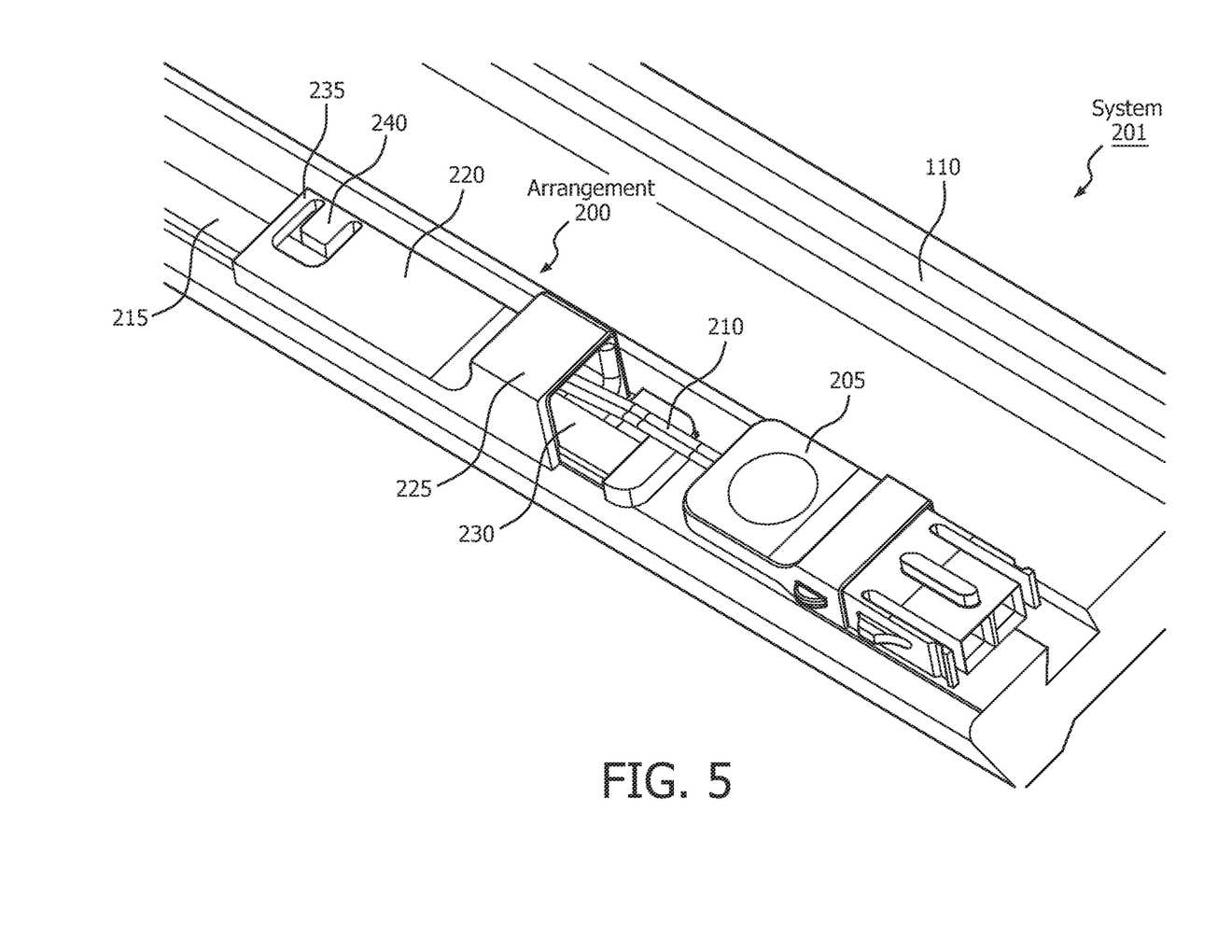
FIG. 5 shows a second perspective view of the arrangement of FIG. 2 according to the exemplary embodiments.
Figure 6:
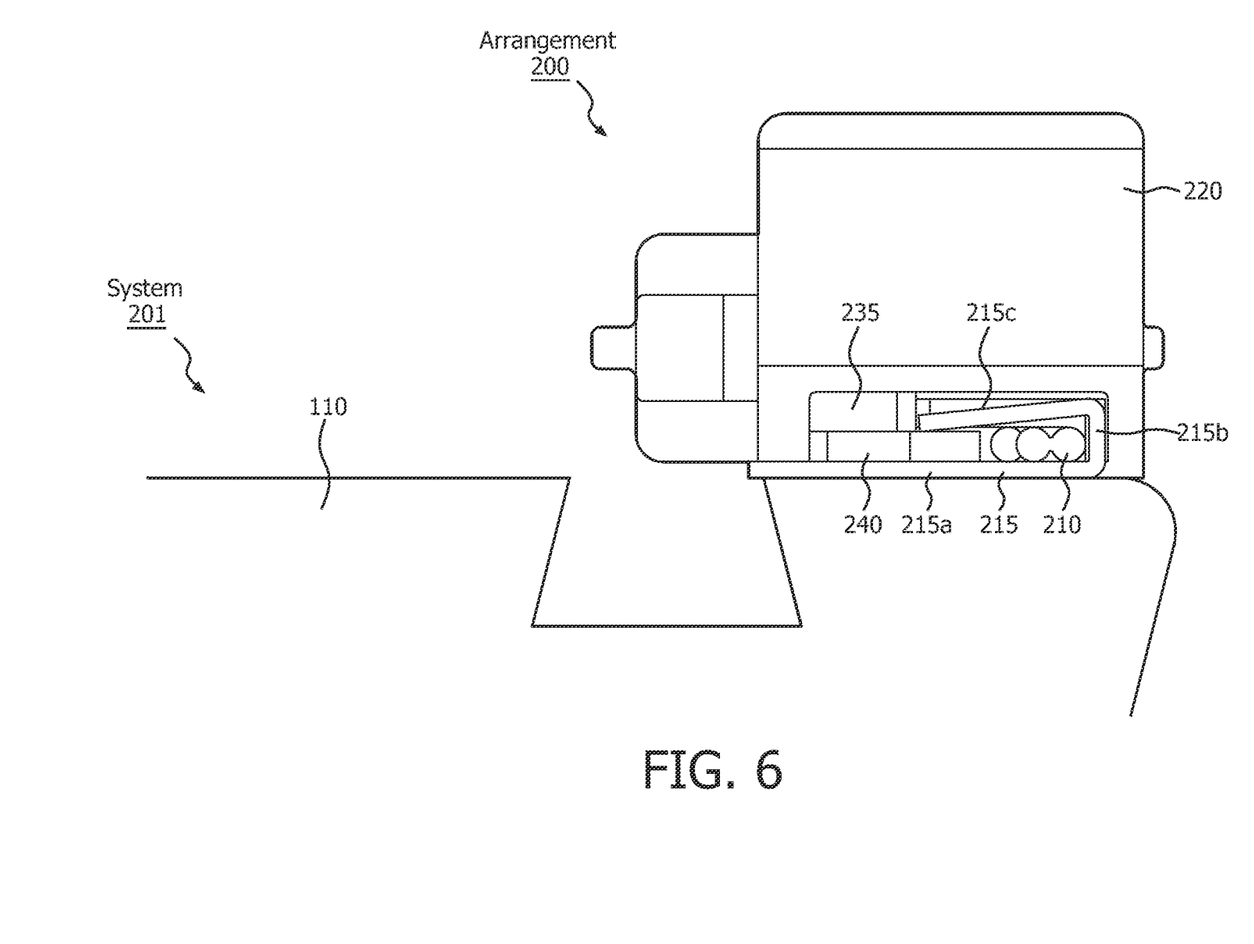
FIG. 6 shows a cross sectional view of the arrangement of FIG. 2 according to the exemplary embodiments.

FIGS. 2-6 show an arrangement 200 used with a patient table 110 according to the exemplary embodiments. Specifically, FIG. 2 shows an overall view of the arrangement 200 incorporated into the patient table 110; FIG. 3 shows an overhead view of the arrangement 200; FIG. 4 shows a first perspective view of the arrangement 200; FIG. 5 shows a second perspective view of the arrangement 200; and FIG. 6 shows a cross sectional view of the arrangement 200. The combination of the arrangement 200 with the patient table 110 is represented as a system 201.

As illustrated in the overall view of FIG. 2, the patient table 110 may include a top surface 110*a* with various features. One feature of the top surface 110*a* of the patient table 110 may be a central area 110*b* between longer sides 110*c* in which a patient lies. Another feature of the top surface 110*a* of the patient table 110 may be peripheral shapes 110*d* (e.g., recesses) along the longer sides 110*c*. These peripheral shapes 110*d* may correspond to further shapes in the capturing device 105 so that the patient table 110 is moved into and out of the bore along a known trajectory. The arrangement 200 may be located along a side of the patient table 110 (e.g., longer sides 110c), specifically along an outer edge of the side outside the peripheral shapes 110d on that same side to not interfere with the peripheral shapes 110d. Furthermore, the arrangement 200 may be located along the top surface 110a of the patient table 110.

It should be noted that the position of the arrangement 200 being on the top surface 110a and along one of the long sides 110c of the patient table 110 is only exemplary. As will become clearer from the description below, the arrangement 200 may be positioned along any surface of the patient table 110 as long as the cable housed therein is capable of providing the connection between the capture device 105 and the coil panel 125. For example, the arrangement 200 may be positioned on a side surface along a long side of the patient table 110. In another example, the arrangement 200 may be positioned on a bottom surface along a short side of the patient table 110. It should also be noted that the arrangement 200 may be positioned on any other component and not necessarily the patient table 110.

As illustrated, the arrangement 200 may be configured for a cable 210 including a connector 205. The connector 205 may be shaped and sized to couple to a corresponding connector of the coil panel 125. Thus, when the patient is lying on the patient table 110, the coil panel 125 may be placed in the proper position relative to the patient body. Subsequently, the connector 205 may be coupled to the coil panel 125. The connector 205 may include a locking arrangement such as biased legs 205a that may be moved toward one another when being coupled to the corresponding connector of the coil panel 125. The legs 205a may bias away from each other so that an extending component is pushed into a recess of the corresponding connector. The locking arrangement may unlock the connector 205 from the corresponding connector of the coil panel 125 from being pushed toward each other and pulled out of the corresponding connector. It should be noted that the connector 205 and the use thereof as well as the locking arrangement type and use are only exemplary. For example, the cable 210 may be permanently coupled to the coil panel 125.

The arrangement 200 may also be aligned along the long side 110c of the patient table 110 such that the connector 205 is on a common short side of the patient table 110 as where the head of the patient is located when lying thereon. However, it should also be noted that such an alignment is only exemplary. Those skilled in the art will understand that the arrangement 200 may be in an opposite manner or may be in different alignments such as perpendicular to the above noted manner.

As discussed above, the cable 210 may be an optical data cable. Although FIG. 2 is not necessarily drawn to scale, the cable 210 may have a size that is relatively small compared to the patient table 110 and the connector 205. As will be more evident below, the size of the cable 210 may impact the size and shape of the other components of the arrangement 200. It should again be noted that the cable 210 being an optical data cable is only exemplary. For example, if the cable 210 were to only provide a tethering functionality, the cable 210 may be a chain, a rope, etc.

The arrangement 200 may further include a slot 215 and a slider 220. The slot 215 may extend the length of the arrangement 200. Although the slot 215 is described herein as an extended recess component, this configuration of the slot 215 is only exemplary. For example, the slot 215 may be any recess or pocket that is capable of housing the cable 210. The slot 215 may be manufactured with any material not subject to magnetism when the capturing device 105 is a MRI device. However, the material with which the slot 215 is manufactured may also be based upon any restrictions there may be in manufacturing materials for the imaging device 105. The slot 215 may also be elastic or may be biased to return to an original shape. As will be discussed in further detail below, the cable 210 may be housed in the slot 215 through an opening that has a smaller size than the cable 210. Thus, the opening of the slot 215 may be extended temporarily for the cable 210 to be inserted/removed.

Specifically, as shown in FIG. 6, the cross-sectional view illustrates a relative size of the cable 210 relative to the slot 215 and the opening thereof. The slot 215 may have a sideways J-shape cross section. Specifically, the slot 215 may include a first wall 215a extending from a first free end to a second end along an entire lateral distance of the slot 215. The slot 215 may also include a second wall 215b extending perpendicularly away from the first wall 215a in which a first end of the second wall 215b is coupled (e.g., permanently) to the second end of the first wall 215a. The slot 215 may further include a third wall 215c extending angularly away from the second wall 215b in a common direction as the first wall 215a in which a first end is free and the second end is coupled (e.g., permanently) to the second end of the second wall 215b.

The angular extension of the third wall 215c may create an opening with the first wall 215a for the slot 215. Specifically, the opening may be present at the first end of the third wall 215c. Since the slot 215 is coupled to the top surface of the patient table 110, the third wall 215c and/or the second wall 215b may be configured with the elastic biasing functionality so that the opening is extended slightly to receive the cable 210. As shown, the cable 210 may include two (2) cables with circular cross sections. A diameter of the circular cross section may be greater (even only slightly) compared to the opening of the slot 215. When there is no force applied to the extension, the slot 215 may return to the original shape as shown in FIG. 6. It is noted that the angular extension of the third wall 215c also results in the opening being of a lesser size than the second wall 215b. It is also noted that the third wall 215c may have substantially half a length of the first wall 215a while the second wall 215b may have substantially a third of the length of the third wall 215c.

It should be noted that the above configuration and use of the slot 215 is only exemplary. For example, the relative lengths of the walls 215a-c may depend upon the cable 215 such as with a larger cable, the second wall 215b may be of a greater length. The angular extension of the third wall 215c is also only exemplary. The third wall 215c may, for example, extend substantially perpendicularly away from the second wall 215b so long as the cable 210 may be retained within the slot 215. The first wall 215a being of a greater length than the third wall 215c is also only exemplary. In other exemplary embodiments, the first wall 215a may be of equal or lesser length than the third wall 215c so long as the functionality of the slot 215 is not substantially altered.

With particular regard to the overhead view of FIG. 3, the cable 210 is shown in both its position out of the slot 215 (at area 210a) and within the slot 215 (at area 210b). Specifically, when out of the slot 215, the cable 210 protrudes beyond the length of the third wall 215c. However, when within the slot 215, the cable 210 does not protrude any distance beyond the length of the third wall 215c.

With particular regard to the perspective views of FIGS. 4 and 5, the slider 220 may be a component that enables a smooth transition of the cable 210 to be housed within the slot 215. The slider 220 is described herein as a zipper-type component that moves along a length of the slot 215. However, this mechanism of the slider 220 is only exemplary. Those skilled in the art will understand that the slider 220 may be any movable component that assists in placing the cable 210 into the slot 215. Since the slider 220 moves along the length of the slot 215, the slider 220 may be shaped and sized accordingly. Again referring to the cross-sectional view of FIG. 6, the slider 220 may include an extension or pusher 240 that extends into the slot 215. That is, the extension or pusher 240 may extend beyond the opening of the slot 215 and thereinto. The slider 220 may also include a wall adjacent the second wall 215b so that the slider 220 is incapable of being pushed or pulled laterally relative to the slot 215 which may inadvertently remove the slider 220 along the longitudinal path.

The slider 220 may include a grip 225. The grip 225 may provide a component that is held by the user to move the slider 220 along the length of the slot 215. The slider 220 may also be designed in such a way that the grip 225 provides a first recess 230 to be formed. The first recess 230 may be an opening in the slider 220 from which the cable 210 extends out. Any portion of the cable 210 further away from this first recess 230 may be within the walls of the slider 220 such as below the top surface of the slider 220. The slider 220 may also include a second recess 235 on an opposite end of the first recess 230 for the cable 210 to exit. The second recess 235 may be positioned to cooperate with the extension or pusher 240. The extension or pusher 240 has already been described as a component that holds the slider 220 in a proper position relative to the slider 215. However, the extension or pusher 240 may also provide the zipping functionality. Specifically, the extension or pusher 240 may push or "zip" the cable 210 through the opening and into the slot 215. Thus, when the cable 210 along a portion beyond the first recess 230 is freed from the slot 210 and is to return into the slot 210, the slider 220 may be moved toward a direction of the connector 205. The cable 210 may be pre-positioned with the first recess 230 and prepared for the extension or pusher 240 to move the cable into the slot 215.

It should be noted that the shape and size of the slider 220 as well as its components are only exemplary. Again, the slider 220 may be any component that is movable along the length of the slot 215. The zipping mechanism described above for the slider 220 is only exemplary in the manner in which the cable 210 becomes housed in the slot 215. Specifically, the use of the extension or pusher 240 or any comparable component is only exemplary. The moving functionality of the slider 220 is also only exemplary. As the slider 220 may represent any component that is configured to move the cable 210 from a freed position to a housed position, the mechanism with which the slider 220 operates is only exemplary since any component that performs the overall function of housing the cable 210 may be used.

It should also be noted that the use of the slider 220 is only exemplary. When the slider 220 is not provided, the slot 215 may still be used to house the cable 210. For example, if the cable 210 is large enough, the user may push the cable 210 into the slot 215. Specifically, the user may push the cable 210 along the length of the slot 215 until the portions of the cable that are intended to be therein are fully housed.

In an exemplary manner of using the arrangement 200, the cable 210 may be substantially wholly within the slot 215. Accordingly, a small portion of the cable 210 may be freed such as shown in FIG. 2. The connector 205 which is coupled to an end of the cable 210 may also be near the slider 220 as shown in FIG. 2. It is noted that the opposite end of the cable 210 may be coupled to the capturing device 105 such as to the control panel 115. While the arrangement 200 is in this configuration, the patient may be free to move onto the patient table 110 without consideration of possibly becoming tangled or inadvertently displacing the cable 210.

Once the patient is lying on the patient table 110, the technician or user may place the coil panel 125 over the appropriate body part of the patient. Because the coil panel 125 may be placed anywhere, the coil panel 125 may have a flexible design to wrap around a body part such as an arm or leg or may have a less flexible, rigid design to be placed on the chest. Once the coil panel 125 is placed, the user may move the slider 220 using the grip 225 to begin freeing a greater portion of the cable 210. Specifically, the slider 220 may be moved along the slot 215 in a direction away from the connector 205.

It should be noted that the freeing of the cable 210 may be performed in a variety of manners. In a first example, the slider 210 may include a "puller" that performs a substantially opposite effect than the pusher 240. That is, the puller may move the cable 210 out of the slot 215. In a second example, the slider 210 may simply be moved out of the way for the user to pull the connector in a particular direction (e.g., away from the second wall 215b) to manually remove the cable 210 from within the slot 215.

Once the user has moved the slider 220 a sufficient distance to free enough of the cable 210, the user may couple the connector 205 to the corresponding connector of the coil panel 125. It should be noted that the slider 220 may provide yet another functionality. Specifically, the slider 220 may determine the length of the cable that is freed from the slot 215. Using the manual removal of the cable 210, the slider 220 may prevent the user from freeing any more of the cable 210 from the slot 215 unless the slider 220 is moved further. Once this is accomplished, the capturing device 105 is prepared for use. For example, the user may use the control panel 115 to move the patient table into the bore of the capturing device 105. The user may then move into the operator room 130 and use the imaging device 135 to begin the capturing procedure.

After the capturing procedure is completed, the user may return to the capturing device 105. Via the control panel 115, the patient table 110 may be moved out of the bore of the capturing device 105. The connector 205 may be decoupled from the coil panel 125 (e.g., pushing the biased legs toward one another and being pulled out). The coil panel 125 may be removed from the patient and placed in a different location. The user may then begin move the slider 220 back toward the connector 205. While being moved in this direction, the pusher 240 may place the cable 210 into the slot 215. Once the cable 210 has been safely housed in the slot 215, the patient may be free to move off the patient table 110, again without consideration of becoming tangled or inadvertently displacing the cable 210.

Figure 7:
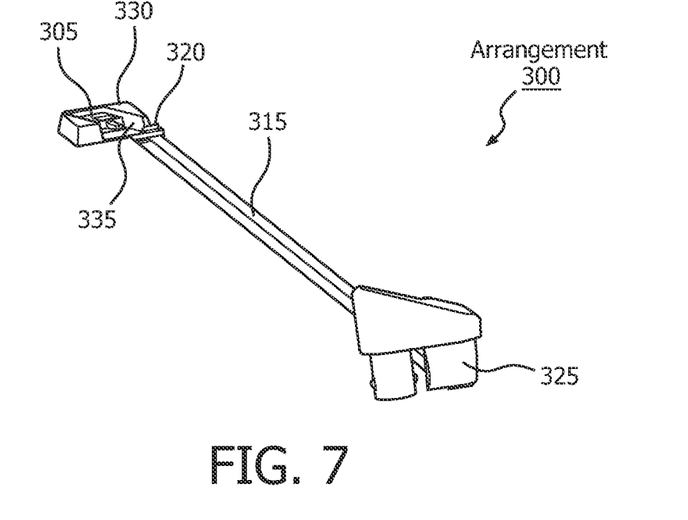
FIG. 7 shows a further arrangement according to the exemplary embodiments.
Figure 8:
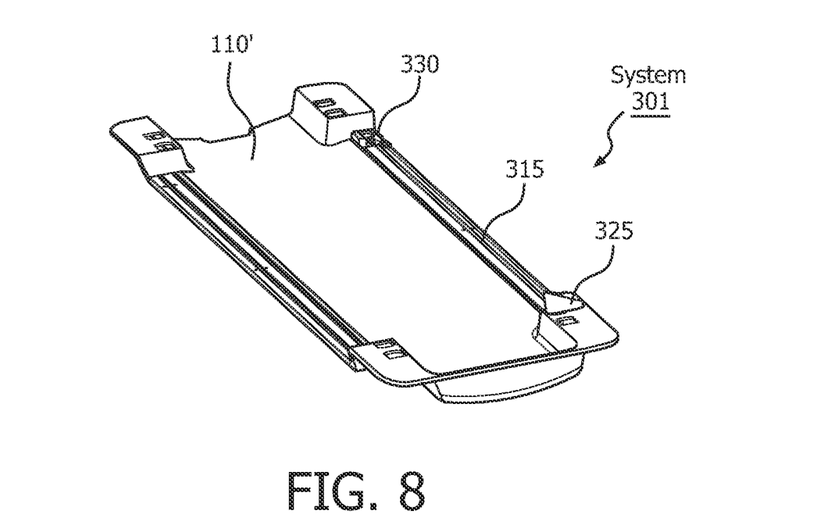
FIG. 8 shows an overall view of the further arrangement of FIG. 7 incorporated into a patient table according to the exemplary embodiments.
Figure 9:
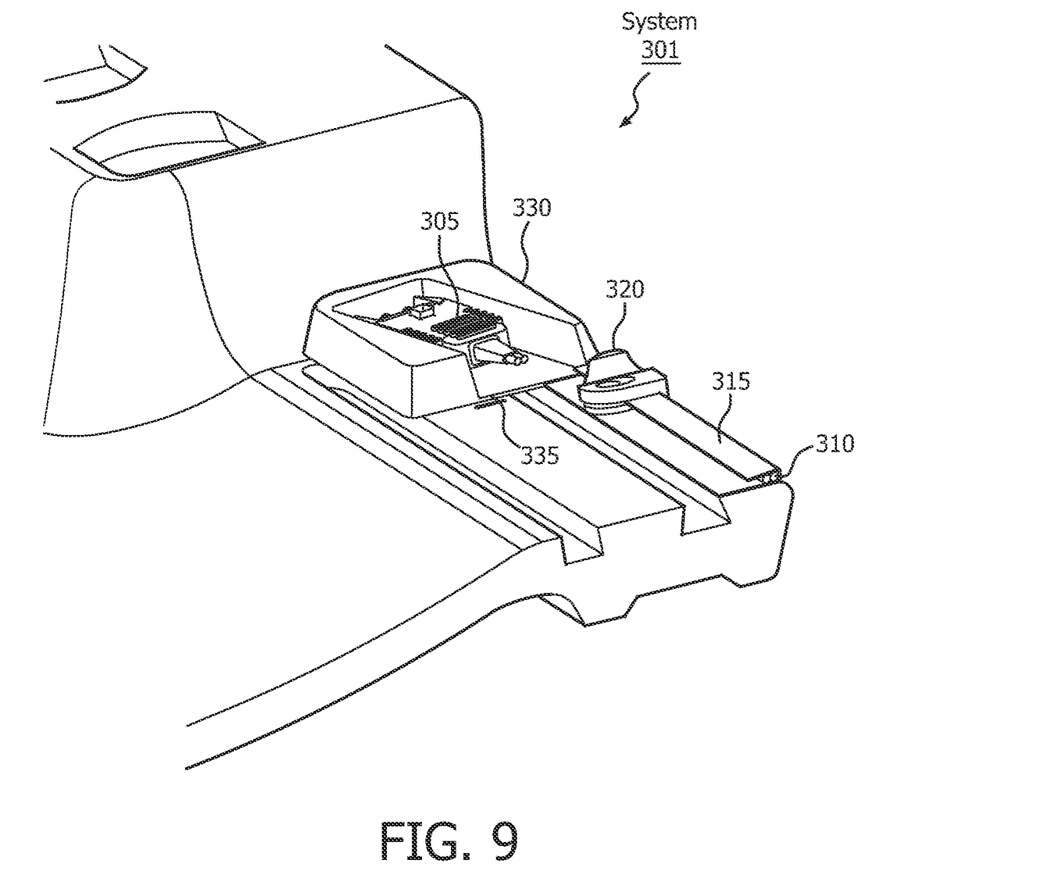
FIG. 9 shows a focused view of the further arrangement of FIG. 7 according to the exemplary embodiments.

FIGS. 7-9 show a further arrangement 300 according to the exemplary embodiments. Specifically, the further arrangement 300 may include components that aid in placing the arrangement 300 onto a patient table. FIG. 7 shows the different components of the further arrangement 300. FIG. 8 shows an overall view of the further arrangement 300 incorporated into a patient table according to the exemplary embodiments. FIG. 9 shows a focused view of the further arrangement 300. The combination of the further arrangement 300 with the patient table is represented as a system 301.

The arrangement 300 may include substantially similar components as the arrangement 200. Specifically, the arrangement 300 may include a connector 305, a cable 310, a slot 315, and a slider 320. These components may all be substantially similar to the counterparts in the arrangement 200. However, the arrangement 300 may further include a lock 325, a holder 330, and a pocket 335. The lock 325 may include an extension sized and shaped to couple to a recess or corresponding component on the patient table 110'. As shown in FIG. 8, the patient table 110' may include a plurality of recesses on the corners of the table 110'. The lock 325 may couple to one of these recesses to couple the arrangement 300 to the patient table 110'. It should be noted that there may be a further lock (not shown) on an opposite side of the arrangement 300 to also lock this opposite side. However, when no further lock is used, the slot 315 may be made with a sufficiently rigid material along the longitudinal length to maintain the positioning of the arrangement 300 on the patient table 110'.

The holder 330 may be a component located at the opposite end of the arrangement 300 relative to the lock 325. The holder 330 may include the pocket 335 which may be a recess. With particular regard to FIG. 9, the pocket 335 may be sized and shaped to hold the connector 305 while still providing enough space for the user to remove the connector from the pocket 335. The holder 330 may be a further measure for safely housing the cable 310 and the connector 305 from any inadvertent displacement. That is, when the connector 305 is housed within the pocket 335 of the holder 330, the patient may move onto or off the patient table 110' without consideration of displacing the cable 310 (via the slot 315) or the connector 305 (via the pocket 335).

According to the exemplary embodiments, an arrangement and system of placing an external cable into a slot to prevent damage thereto and maintain connections of the external cable between two components is provided. The slot may safely house the cable therein until needed when it is removed therefrom. When no longer needed, the cable may be placed back into the slot for safety and reliability purposes. The arrangement may further include a slider that aids in placing the cable into the slot while also determining an amount of cable that is freed from the slot for use.

It will be apparent to those skilled in the art that various modifications may be made in the present invention, without departing from the spirit or the scope of the invention. Thus, it is intended that the present invention cover modifications and variations of this invention provided they come within the scope of the appended claims and their equivalent.

What is claimed is:

1. An arrangement configured to be secured to a patient table, the arrangement comprising:
a slot extending from a first end to a second end, the slot including a recess configured to receive a cable therein; and
a movable component configured to slide along a length of the slot, the movable component including a first end and a second end, wherein the movable component includes an extension that extends into the slot;
wherein sliding of the movable component along the slot in a first direction frees a first portion of the cable from the slot and sliding of the movable component along the slot in a second direction opposite the first direction causes the movable component to align the cable with the slot and the extension to insert the cable into the slot.

2. The arrangement of claim 1, wherein the slot is J-shaped including a first wall, a second wall, and a third wall, the first wall configured to couple onto a surface of the patient table, the second wall extending from the first wall in a first direction away from the surface, the third wall extending from the second wall in a second direction along the surface, the first wall and the third wall creating an opening for the recess.

3. The arrangement of claim 2, wherein the movable component includes a first recess on its first end and a second recess on its second end, the cable being housed within the movable component between the first and second recesses.

4. The arrangement of claim 2, wherein the extension extends through the opening into the recess.

5. The arrangement of claim 4, wherein the movable component includes a portion adjacent the third wall configured to prevent the movable component from being removed out of the recess.

6. The arrangement of claim 4, wherein the third wall extends in the second direction angled toward the first wall such that the opening is of lesser size than the second wall and the extension extends the opening to receive the cable.

7. The arrangement of claim 1, further comprising:
a connector coupled to an end of the cable.

8. The arrangement of claim 7, further comprising:
a housing including a pocket configured to receive the connector when the movable component is moved to a predetermined position.

9. The arrangement of claim 1, wherein the cable is an optical data cable.

10. The arrangement of claim 1, wherein the slot has an opening that is of lesser size than the cable and the extension elastically enlarges the opening to free the first portion of the cable when the movable component slides in the first direction and to push the cable into the slot when the movable component slides in the second direction.

11. A system, comprising:
a patient table configured to move into and out of a bore of an imaging capturing device;
a cable; and
an arrangement secured to the patient table, the arrangement including:
a slot extending from a first end to a second end and configured to receive the cable therein; and
a movable component configured to slide along a length of the slot, the movable component including a first end and a second end, wherein the movable component includes an extension that extends into the slot,
wherein sliding of the movable component along the slot in a first direction frees a first portion of the cable from the slot and sliding of the movable component along the slot in a second direction opposite the first direction causes the movable component to align the cable with the slot and the extension to push the cable into the slot.

12. The system of claim 11, wherein the cable extending beyond the first end of the movable component is free of the slot, the cable extending beyond the second end of the movable component is housed within the slot.

13. The system of claim 11, further comprising:
a connector coupled to an end of the cable; and
a housing including a pocket configured to receive the connector when the movable component is moved to a predetermined position.

14. The system of claim 11, wherein the cable is an optical data cable.

15. The system of claim 11, wherein the slot has an opening that is of lesser size than the cable and the extension elastically enlarges the opening to free the first portion of the cable when the movable component slides in the first direction and to push the cable into the slot when the movable component slides in the second direction.

16. A system comprising:
a patient table configured to move into and out of a bore of an imaging capturing device;
a cable; and
an arrangement secured to the patient table, the arrangement including:
a slot extending from a first end to a second end and configured to receive the cable therein, wherein the slot is J-shaped defined by a first wall, a second wall, and a third wall, the first wall configured to couple the arrangement onto a surface of the patient table, the second wall extending from the first wall in a first direction away from the surface, the third wall extending from the second wall in a second direction along the surface, the first wall and the third wall creating an opening for the slot; and
a movable component configured to slide along a length of the slot, the movable component including a first end and a second end, wherein the movable component includes an extension that extends into the slot,
wherein sliding of the movable component along the slot in a first direction frees a first portion of the cable from the slot and sliding of the movable component along the slot in a second direction opposite the first direction causes the movable component to align the cable with the slot and the extension to push the cable into the slot.

17. The system of claim 16, wherein the movable component includes a first recess on its first end and a second recess on its second end, the cable being housed within the movable component between the first and second recesses.

18. The system of claim 17, wherein the movable component includes a portion adjacent the third wall configured to prevent the movable component from being removed out of the slot.

19. The system of claim 16, wherein the third wall extends in the second direction angled toward the first wall, the opening being lesser in size than the cable and wherein the extension is configured to enlarge the opening and push the cable into the slot when the movable component slides in the second direction and frees the first portion of the cable when the movable component slides in the first direction.

20. A Magnetic Resonance Imaging (MRI) device, comprising:
a patient table configured to move into and out of a bore of the MRI device;
a cable including first and second ends, the first end coupled to a connector, the second end coupled to the MRI device;
a slot coupled to the patient table extending from a first end to a second end and configured to receive the cable therein; and
a zipper-type component configured to slide along a length of the slot, the zipper-type component including a first end and a second end, the cable extending beyond the first end of the zipper-type component being free of the slot the cable extending beyond the second end of the zipper-type component being housed within the slot, wherein the zipper-type component includes a pusher extension that extends into the slot and contacts the cable, and sliding of the zipper-type component along the slot in a first direction frees a first portion of the cable from the slot and sliding of the zipper-type component along the slot in a second direction opposite the first direction causes the zipper-type component to align the cable with the slot and the pusher extension to push the cable into the slot.

21. The MRI device of claim 20, wherein the cable is an optical data cable.

22. The MRI device of claim 20, wherein the slot has an opening that is of lesser size than the cable and the extension elastically enlarges the opening to free the first portion of the cable when the movable component slides in the first direction and pushes the cable into the slot when the movable component slides in the second direction.

23. The MRI device of claim 20, wherein the slot is J-shaped including a first wall, a second wall, and a third wall, the first wall configured to couple the arrangement onto a top surface of the patient table, the second wall extending from the first wall in a first direction away from the surface, the third wall extending from the second wall in a second direction along the surface, the first wall and the third wall creating an opening for the slot.

* * * * *